United States Patent [19]
Jones et al.

[11] Patent Number: 5,840,511
[45] Date of Patent: Nov. 24, 1998

[54] METHODS COMPRISING CALCIUM INDEPENDENT CYTOSOLIC PHOSPHOLIPASE A/B ENZYMES

[75] Inventors: Simon Jones, Somerville; Jin Tang, Canton, both of Mass.

[73] Assignee: Genetics Institute, Inc., Cambridge, Mass.

[21] Appl. No.: 735,716

[22] Filed: Oct. 23, 1996

Related U.S. Application Data

[60] Continuation of Ser. No. 422,106, Apr. 14, 1995, Pat. No. 5,589,170, which is a division of Ser. No. 281,193, Jul. 27, 1994, Pat. No. 5,466,595.

[51] Int. Cl.$^6$ ............................. C12Q 1/44; A61K 38/46
[52] U.S. Cl. ........................... 435/19; 424/94.6; 435/198
[58] Field of Search ............................. 424/94.6; 435/19, 435/198

[56] References Cited

U.S. PATENT DOCUMENTS

| | | | |
|---|---|---|---|
| 5,322,776 | 6/1994 | Knopf et al. | 435/69.1 |
| 5,328,842 | 7/1994 | Chiou et al. | 435/240.2 |
| 5,354,677 | 10/1994 | Knopf et al. | 435/198 |
| 5,466,595 | 11/1995 | Jones et al. | 435/240.2 |

OTHER PUBLICATIONS

Aarsman et al., J. Biol. Chem. 264:10008 (1989).
Ackermann et al., FASEB J. 7:1237(1993).
Ackermann et al., J. Biol. Chem. 269:9227 (1994).
Angle et al., Biochim. et Biophys. Acta 962:234 (1988).
Cao et al., J. Biol. Chem. 262:16927 (1987).
Ford et al., J. Clin. Invest. 88:331 (1991).
Gassama–Diagne et al., J. Biol. Chem. 264:9470 (1989).
Gross, TCM 2:115 (1992).
Gross et al., Biochemistry 32:327 (1993).
Hazen et al., J. Biol. Chem. 268:9892 (1993).
Hazen et al., J. Biol. Chem. 265:10622 (1990).
Hazen et al., J. Biol. Chem. 266:14526 (1991).
Hazen et al., Meth. in Enzymol. 197:400 (1991).
Hazen et al., J. Clin. Invest. 91:2513 (1993).
Hazen et al., J. Biol. Chem. 266:7227 (1991).
Hazen et al., Circulation Research 70:486 (1992).
Hazen et al., J. Biol. Chem. 266:5629 (1991).
Hirashima et al., J. Neurochem. 59:708 (1992).
Kanda et al., Biochem. and Biophys Res. Comm. 163:42 (1989).
Kramer et al., J. Biol. Chem. 264:5768 (1989).
Lehman et al., J. Biol. Chem. 268:20713 (1993).
Loeb and Gross, J. Biol. Chem. 261:10467 (1986).
Leslie et al., Biochim. et Biophys Acta. 963:476 (1988).
Nijssen et al., Biochim. et Biophys Acta 876:611 (1986).
Pierik et al., Biochim. et Biophys Acta 962:345 (1988).
Ramanadham et al., Biochemistry 33:7442 (1994).
Ramanadham et al., Biochemistry 32:337 (1993).
Ross et al., Archives of Biochem. and Biophys. 238:247 (1985).
Seilhamer et al., J. Biol. Chem. 264:5335 (1989).
Ueda et al., Biochem. and Biophys. Res. Comm. 195:1272 (1993).
Ulevitch et al., J. Biol. Chem. 263:3079 (1988).
Wolf and Gross, J. Biol. Chem. 260:7295 (1985).
Yost et al., Biochem. International 24:199 (1991).
Zupan et al., J. Med. Chem. 36:95 (1993).
Zupan et al., J. Biol. Chem. 267:8707 (1992).
Zupan et al., FEBS 23427 (1991).
Clark, J.D. (1991) "A novel arachidonic acid–selective cytosolic PLA$_2$ contains a Ca$^{2+}$–dependent translocation domain with homology to PKC and GAP" *Cell* 65:1043–1051.
Sharp, J.D. et al. (1991) "Molecular cloning and expression of human Ca$^{2+}$–sensitive cytosolic phospholipase A$_2$" *J. Biol. Chem.* 266(23):14850–14853.
Han, J. H. et al. (1987) "Isolation of full–length putative rat lysophospholipase cDNA using improved methods for mRNA isolation and cDNA cloning" *Biochemistry* 26:1617–1625.
Dennis, E.A. (1994) "Diversity of group types, regulation, and function of phospholipase A2" *J. Biol. Chem.* 269(18):13057–13060, May 1994.

*Primary Examiner*—Robert A. Wax
*Assistant Examiner*—Kawai Lau
*Attorney, Agent, or Firm*—Genetics Institute, Inc.; Scott A. Brown

[57] ABSTRACT

The invention provides a novel calcium-independent cytosolic phospholipase A$_2$/B enzyme, polynucleotides encoding such enzyme and methods for screening unknown compounds for anti-inflammatory activity mediated by the arachidonic acid cascade.

4 Claims, 7 Drawing Sheets

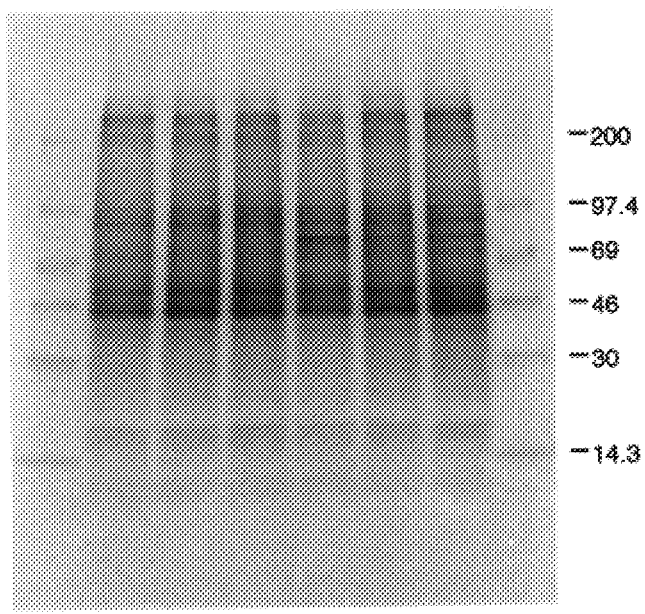

SEQUENCE LISTING ( 1 ) GENERAL INFORMATION:

( i i i ) NUMBER OF SEQUENCES: 15

( 2 ) INFORMATION FOR SEQ ID NO: 1:

( i ) SEQUENCE CHARACTERISTICS:
( A ) LENGTH: 2935 base pairs
( B ) TYPE: nucleic acid
( C ) STRANDEDNESS: double
( D ) TOPOLOGY: linear ( i i ) MOLECULE TYPE: cDNA ( i i i ) HYPOTHETICAL: NO ( i i i ) ANTI-SENSE: NO ( i x ) FEATURE:
( A ) NAME/KEY: CDS
( B ) LOCATION: 96..2352

( x i ) SEQUENCE DESCRIPTION: SEQ ID NO: 1:

```
GCGGCCGCGT CGACGAAGTA AGCGGGCGGA GAAGTGCTGA GTAAGCCGAG AGTAAGGGGG                    60

CAGGCTGTCC CCCCCCCCA CCTGCCCCAC GGAGG ATG CAG TTC TTC GGA CGC                      113
                                       Met Gln Phe Phe Gly Arg
                                         1               5

CTT GTC AAC ACC CTC AGT AGT GTC ACC AAC TTG TTC TCA AAC CCA TTC                     161
Leu Val Asn Thr Leu Ser Ser Val Thr Asn Leu Phe Ser Asn Pro Phe
             10                  15                  20

CGG GTG AAG GAG ATA TCT GTG GCT GAC TAT ACC TCA CAT GAA CGT GTT                     209
Arg Val Lys Glu Ile Ser Val Ala Asp Tyr Thr Ser His Glu Arg Val
         25                  30                  35

CGA GAG GAA GGG CAG CTG ATC CTG TTC CAG AAT GCT TCC AAT CGC ACC                     257
Arg Glu Glu Gly Gln Leu Ile Leu Phe Gln Asn Ala Ser Asn Arg Thr
     40                  45                  50

TGG GAC TGC ATC CTG GTC AGC CCT AGG AAC CCA CAT AGT GGC TTC CGA                     305
Trp Asp Cys Ile Leu Val Ser Pro Arg Asn Pro His Ser Gly Phe Arg
 55                  60                  65                  70

CTC TTC CAG CTG GAG TCA GAG GCA GAT GCC CTG GTG AAC TTC CAG CAG                     353
Leu Phe Gln Leu Glu Ser Glu Ala Asp Ala Leu Val Asn Phe Gln Gln
                 75                  80                  85

TTC TCC TCC CAG CTG CCA CCC TTC TAC GAG AGC TCT GTG CAG GTC CTG                     401
Phe Ser Ser Gln Leu Pro Pro Phe Tyr Glu Ser Ser Val Gln Val Leu
             90                  95                 100

CAT GTG GAG GTG CTG CAG CAC CTG TCT GAC CTG ATC CGA AGC CAC CCC                     449
His Val Glu Val Leu Gln His Leu Ser Asp Leu Ile Arg Ser His Pro
            105                 110                 115

AGC TGG ACG GTG ACA CAC CTG GCG GTG GAG CTT GGC ATT CGG GAG TGC                     497
Ser Trp Thr Val Thr His Leu Ala Val Glu Leu Gly Ile Arg Glu Cys
        120                 125                 130

TTC CAC CAC AGC CGC ATC ATC AGC TGC GCC AAC AGC ACA GAG AAT GAG                     545
Phe His His Ser Arg Ile Ile Ser Cys Ala Asn Ser Thr Glu Asn Glu
135                 140                 145                 150

GAG GGC TGC ACC CCA CTG CAT TTG GCA TGC CGC AAG GGT GAC AGT GAG                     593
Glu Gly Cys Thr Pro Leu His Leu Ala Cys Arg Lys Gly Asp Ser Glu
                155                 160                 165
```

```
ATC CTG GTG GAG TTG GTA CAG TAC TGC CAT GCC CAA ATG GAT GTC ACT    641
Ile Leu Val Glu Leu Val Gln Tyr Cys His Ala Gln Met Asp Val Thr
            170             175                 180

GAC AAC AAA GGA GAG ACG GCC TTC CAT TAC GCT GTA CAA GGG GAC AAT    689
Asp Asn Lys Gly Glu Thr Ala Phe His Tyr Ala Val Gln Gly Asp Asn
        185                 190                 195

TCC CAG GTG CTG CAG CTC CTA GGA AAG AAC GCC TCA GCT GGC CTG AAC    737
Ser Gln Val Leu Gln Leu Leu Gly Lys Asn Ala Ser Ala Gly Leu Asn
    200                 205                 210

CAG GTG AAC AAA CAA GGG CTA ACT CCA CTG CAC CTG GCC TGC CAG ATG    785
Gln Val Asn Lys Gln Gly Leu Thr Pro Leu His Leu Ala Cys Gln Met
215                 220                 225                 230

GGG AAG CAG GAG ATG GTA CGC GTC CTG CTG CTT TGC AAT GCC CGC TGC    833
Gly Lys Gln Glu Met Val Arg Val Leu Leu Leu Cys Asn Ala Arg Cys
                235                 240                 245

AAC GTC ATG GGA CCC AGT GGC TTT CCC ATC CAC ACA GCC ATG AAG TTC    881
Asn Val Met Gly Pro Ser Gly Phe Pro Ile His Thr Ala Met Lys Phe
            250                 255                 260

TCC CAG AAG GGG TGT GCT GAA ATG ATT ATC AGC ATG GAC AGC AGC CAG    929
Ser Gln Lys Gly Cys Ala Glu Met Ile Ile Ser Met Asp Ser Ser Gln
        265                 270                 275

ATC CAC AGC AAG GAT CCT CGC TAT GGA GCC AGC CCG CTC CAC TGG GCC    977
Ile His Ser Lys Asp Pro Arg Tyr Gly Ala Ser Pro Leu His Trp Ala
    280                 285                 290

AAG AAT GCC GAG ATG GCC CGG ATG CTG CTG AAG CGG GGA TGT GAT GTG   1025
Lys Asn Ala Glu Met Ala Arg Met Leu Leu Lys Arg Gly Cys Asp Val
295                 300                 305                 310

GAC AGC ACA AGC GCT GCG GGG AAC ACA GCC CTG CAT GTG GCA GTG ATG   1073
Asp Ser Thr Ser Ala Ala Gly Asn Thr Ala Leu His Val Ala Val Met
                315                 320                 325

CGG AAC CGC TTT GAC TGC GTC ATG GTG CTG CTG ACC TAC GGG GCC AAC   1121
Arg Asn Arg Phe Asp Cys Val Met Val Leu Leu Thr Tyr Gly Ala Asn
            330                 335                 340

GCA GGC ACC CCA GGG GAG CAT GGG AAC ACG CCG CTG CAC CTG GCC ATC   1169
Ala Gly Thr Pro Gly Glu His Gly Asn Thr Pro Leu His Leu Ala Ile
        345                 350                 355

TCG AAA GAT AAC ATG GAG ATG ATC AAA GCC CTC ATT GTA TTT GGG GCA   1217
Ser Lys Asp Asn Met Glu Met Ile Lys Ala Leu Ile Val Phe Gly Ala
    360                 365                 370

GAA GTG GAT ACC CCA AAT GAC TTT GGG GAG ACT CCT GCC TTC ATG GCC   1265
Glu Val Asp Thr Pro Asn Asp Phe Gly Glu Thr Pro Ala Phe Met Ala
375                 380                 385                 390

TCC AAG ATC AGC AAA CAG CTT CAG GAC CTC ATG CCC ATC TCC CGA GCC   1313
Ser Lys Ile Ser Lys Gln Leu Gln Asp Leu Met Pro Ile Ser Arg Ala
                395                 400                 405

CGG AAG CCA GCA TTC ATC CTG AGC TCC ATG AGG GAT GAG AAG CGA ATC   1361
Arg Lys Pro Ala Phe Ile Leu Ser Ser Met Arg Asp Glu Lys Arg Ile
            410                 415                 420

CAT GAT CAC CTG CTC TGC CTG GAC GGA GGG GGC GTG AAA GGC CTG GTC   1409
His Asp His Leu Leu Cys Leu Asp Gly Gly Gly Val Lys Gly Leu Val
        425                 430                 435

ATC ATC CAA CTC CTC ATT GCC ATC GAG AAG GCC TCA GGT GTG GCC ACC   1457
Ile Ile Gln Leu Leu Ile Ala Ile Glu Lys Ala Ser Gly Val Ala Thr
    440                 445                 450

AAG GAC CTC TTC GAC TGG GTG GCA GGA ACC AGC ACT GGG GGC ATC CTG   1505
Lys Asp Leu Phe Asp Trp Val Ala Gly Thr Ser Thr Gly Gly Ile Leu
455                 460                 465                 470

GCC CTG GCC ATT CTG CAC AGT AAG TCC ATG GCC TAT ATG CGT GGT GTG   1553
Ala Leu Ala Ile Leu His Ser Lys Ser Met Ala Tyr Met Arg Gly Val
                475                 480                 485
```

| | | | | | | | | | | | | | | | | |
|---|---|---|---|---|---|---|---|---|---|---|---|---|---|---|---|---|
| TAC | TTC | CGT | ATG | AAA | GAT | GAG | GTG | TTT | CGG | GGC | TCA | CGG | CCC | TAT | GAG | 1601 |
| Tyr | Phe | Arg | Met 490 | Lys | Asp | Glu | Val 495 | Phe | Arg | Gly | Ser | Arg | Pro 500 | Tyr | Glu | |
| TCT | GGA | CCC | CTG | GAG | GAG | TTC | CTG | AAG | CGG | GAG | TTT | GGG | GAG | CAC | ACC | 1649 |
| Ser | Gly | Pro 505 | Leu | Glu | Glu | Phe | Leu 510 | Lys | Arg | Glu | Phe | Gly 515 | Glu | His | Thr | |
| AAG | ATG | ACA | GAT | GTC | AAA | AAA | CCC | AAG | GTG | ATG | CTC | ACA | GGG | ACA | CTG | 1697 |
| Lys | Met 520 | Thr | Asp | Val | Lys | Lys 525 | Pro | Lys | Val | Met | Leu 530 | Thr | Gly | Thr | Leu | |
| TCT | GAC | CGG | CAG | CCA | GCA | GAG | CTC | CAC | CTG | TTC | CGC | AAT | TAC | GAT | GCT | 1745 |
| Ser 535 | Asp | Arg | Gln | Pro | Ala 540 | Glu | Leu | His | Leu | Phe 545 | Arg | Asn | Tyr | Asp | Ala 550 | |
| CCA | GAG | GTC | ATT | CGG | GAA | CCT | CGC | TTC | AAC | CAA | AAC | ATT | AAC | CTG | AAG | 1793 |
| Pro | Glu | Val | Ile | Arg 555 | Glu | Pro | Arg | Phe | Asn 560 | Gln | Asn | Ile | Asn | Leu 565 | Lys | |
| CCG | CCA | ACT | CAG | CCT | GCA | GAC | CAA | CTG | GTA | TGG | CGA | GCA | GCC | CGG | AGC | 1841 |
| Pro | Pro | Thr | Gln 570 | Pro | Ala | Asp | Gln | Leu 575 | Val | Trp | Arg | Ala | Ala 580 | Arg | Ser | |
| AGT | GGG | GCA | GCC | CCA | ACC | TAC | TTC | CGG | CCC | AAT | GGA | CGT | TTC | CTG | GAT | 1889 |
| Ser | Gly | Ala 585 | Ala | Pro | Thr | Tyr | Phe 590 | Arg | Pro | Asn | Gly | Arg 595 | Phe | Leu | Asp | |
| GGT | GGG | CTG | CTG | GCC | AAC | AAC | CCC | ACA | CTA | GAT | GCC | ATG | ACT | GAA | ATC | 1937 |
| Gly | Gly 600 | Leu | Leu | Ala | Asn | Asn 605 | Pro | Thr | Leu | Asp | Ala 610 | Met | Thr | Glu | Ile | |
| CAT | GAA | TAC | AAT | CAG | GAC | ATG | ATC | CGC | AAG | GGC | CAA | GGC | AAC | AAG | GTG | 1985 |
| His 615 | Glu | Tyr | Asn | Gln | Asp 620 | Met | Ile | Arg | Lys | Gly 625 | Gln | Gly | Asn | Lys | Val 630 | |
| AAG | AAA | CTC | TCC | ATA | GTC | GTC | TCT | CTG | GGG | ACA | GGA | AGG | TCC | CCT | CAA | 2033 |
| Lys | Lys | Leu | Ser | Ile 635 | Val | Val | Ser | Leu | Gly 640 | Thr | Gly | Arg | Ser | Pro 645 | Gln | |
| GTG | CCC | GTA | ACC | TGT | GTA | GAT | GTC | TTC | CGC | CCC | AGC | AAC | CCC | TGG | GAA | 2081 |
| Val | Pro | Val | Thr 650 | Cys | Val | Asp | Val | Phe 655 | Arg | Pro | Ser | Asn | Pro 660 | Trp | Glu | |
| CTG | GCT | AAG | ACT | GTT | TTT | GGA | GCC | AAG | GAA | CTG | GGC | AAG | ATG | GTG | GTA | 2129 |
| Leu | Ala | Lys | Thr | Val 665 | Phe | Gly | Ala | Lys | Glu 670 | Leu | Gly | Lys | Met 675 | Val | Val | |
| GAC | TGT | TGC | ACA | GAT | CCA | GAT | GGT | CGG | GCT | GTG | GAC | CGG | GCC | CGG | GCC | 2177 |
| Asp | Cys 680 | Cys | Thr | Asp | Pro | Asp 685 | Gly | Arg | Ala | Val | Asp 690 | Arg | Ala | Arg | Ala | |
| TGG | AGC | GAG | ATG | GTT | GGC | ATC | CAG | TAC | TTC | AGA | CTG | AAC | CCC | CAA | CTA | 2225 |
| Trp 695 | Ser | Glu | Met | Val | Gly 700 | Ile | Gln | Tyr | Phe | Arg 705 | Leu | Asn | Pro | Gln | Leu 710 | |
| GGA | TCA | GAC | ATC | ATG | CTG | GAT | GAG | GTC | AAT | GAT | GCA | GTG | CTG | GTT | AAT | 2273 |
| Gly | Ser | Asp | Ile | Met 715 | Leu | Asp | Glu | Val | Asn 720 | Asp | Ala | Val | Leu | Val 725 | Asn | |
| GCC | CTC | TGG | GAG | ACA | GAA | GTC | TAC | ATC | TAT | GAG | CAC | CGG | GAG | GAG | TTC | 2321 |
| Ala | Leu | Trp | Glu 730 | Thr | Glu | Val | Tyr | Ile 735 | Tyr | Glu | His | Arg | Glu 740 | Glu | Phe | |
| CAG | AAG | CTT | GTC | CAA | ATG | CTG | CTG | TCG | CCC | T | GAGCTCCAGG | CCCTGCTGGC | | | | 2372 |
| Gln | Lys | Leu 745 | Val | Gln | Met | Leu | Leu 750 | Ser | Pro | | | | | | | |

```
AGGGGTGCGC  CAGGCTACCC  AGCACACTGG  GGGCCAAGCT  GGGCCAGGCG  GCTGTGTCTA    2432

CCTGAGGACT  GGGGCTCAGA  GCACAAACAG  GTTCCCACAA  GGCACCTCTC  CTGACCCATC    2492

TGCACTTTGC  CACTCTAGGC  TGAAAGCCCA  GAGTTCCCCT  CAGCCCCTTT  ATGTGACTGT    2552

GAAGGACAAC  TGGCTCCATC  AACTGCCCTA  AATATCAGTG  AGATCAACAC  TAAGGTGTCC    2612

AGTGTACCCA  GAGGGTTCTT  CCAGGGTCCA  TGGCCACCAA  AGCCCACCCC  TTCTTTCCAC    2672

TTCCTGAAGT  CAGTGTCTAC  AGAAATGGAG  TTCCACCCCA  TCATCAGGTG  AAATCCAGGC    2732
```

```
TATTGAAATC  CAGTCTGTTC  GACTTTGCCC  CTCTGCACCT  GCCAATCACC  CCACCCCTGC    2792

AGCCACCCCA  CCTTAAGAGT  CCTCCCAGCT  CTCAAAGGTC  AATCCTGTGC  ATGTACTCTT    2852

CTCTGGAAGG  AGAGTGGGGA  GGGGTTCAAG  GCCACCTCAA  CTGTGAAATA  AATGGGTCTA    2912

GACTCAAAAA  AAAAAAGTCG  ACG                                                2935
```

(2) INFORMATION FOR SEQ ID NO: 2:

(i) SEQUENCE CHARACTERISTICS:
        (A) LENGTH: 752 amino acids
        (B) TYPE: amino acid
        (D) TOPOLOGY: linear (ii) MOLECULE TYPE: protein (xi) SEQUENCE DESCRIPTION: SEQ ID NO: 2:

```
Met  Gln  Phe  Phe  Gly  Arg  Leu  Val  Asn  Thr  Leu  Ser  Ser  Val  Thr  Asn
 1              5                        10                       15

Leu  Phe  Ser  Asn  Pro  Phe  Arg  Val  Lys  Glu  Ile  Ser  Val  Ala  Asp  Tyr
              20                        25                       30

Thr  Ser  His  Glu  Arg  Val  Arg  Glu  Glu  Gly  Gln  Leu  Ile  Leu  Phe  Gln
              35                        40                       45

Asn  Ala  Ser  Asn  Arg  Thr  Trp  Asp  Cys  Ile  Leu  Val  Ser  Pro  Arg  Asn
 50                        55                        60

Pro  His  Ser  Gly  Phe  Arg  Leu  Phe  Gln  Leu  Glu  Ser  Glu  Ala  Asp  Ala
 65                        70                        75                    80

Leu  Val  Asn  Phe  Gln  Gln  Phe  Ser  Ser  Gln  Leu  Pro  Pro  Phe  Tyr  Glu
              85                        90                       95

Ser  Ser  Val  Gln  Val  Leu  His  Val  Glu  Val  Leu  Gln  His  Leu  Ser  Asp
             100                       105                      110

Leu  Ile  Arg  Ser  His  Pro  Ser  Trp  Thr  Val  Thr  His  Leu  Ala  Val  Glu
             115                       120                      125

Leu  Gly  Ile  Arg  Glu  Cys  Phe  His  His  Ser  Arg  Ile  Ile  Ser  Cys  Ala
             130                       135                      140

Asn  Ser  Thr  Glu  Asn  Glu  Glu  Gly  Cys  Thr  Pro  Leu  His  Leu  Ala  Cys
145                       150                       155                  160

Arg  Lys  Gly  Asp  Ser  Glu  Ile  Leu  Val  Glu  Leu  Val  Gln  Tyr  Cys  His
             165                       170                      175

Ala  Gln  Met  Asp  Val  Thr  Asp  Asn  Lys  Gly  Glu  Thr  Ala  Phe  His  Tyr
             180                       185                      190

Ala  Val  Gln  Gly  Asp  Asn  Ser  Gln  Val  Leu  Gln  Leu  Leu  Gly  Lys  Asn
             195                       200                      205

Ala  Ser  Ala  Gly  Leu  Asn  Gln  Val  Asn  Lys  Gln  Gly  Leu  Thr  Pro  Leu
             210                       215                      220

His  Leu  Ala  Cys  Gln  Met  Gly  Lys  Gln  Glu  Met  Val  Arg  Val  Leu  Leu
225                       230                       235                  240

Leu  Cys  Asn  Ala  Arg  Cys  Asn  Val  Met  Gly  Pro  Ser  Gly  Phe  Pro  Ile
             245                       250                      255

His  Thr  Ala  Met  Lys  Phe  Ser  Gln  Lys  Gly  Cys  Ala  Glu  Met  Ile  Ile
             260                       265                      270

Ser  Met  Asp  Ser  Ser  Gln  Ile  His  Ser  Lys  Asp  Pro  Arg  Tyr  Gly  Ala
             275                       280                      285

Ser  Pro  Leu  His  Trp  Ala  Lys  Asn  Ala  Glu  Met  Ala  Arg  Met  Leu  Leu
             290                       295                      300

Lys  Arg  Gly  Cys  Asp  Val  Asp  Ser  Thr  Ser  Ala  Ala  Gly  Asn  Thr  Ala
305                       310                       315                  320
```

-continued

| | | | | | | | | | | | | | | |
|---|---|---|---|---|---|---|---|---|---|---|---|---|---|---|
| Leu | His | Val | Ala | Val<br>325 | Met | Arg | Asn | Arg | Phe<br>330 | Asp | Cys | Val | Met | Val<br>335 | Leu |
| Leu | Thr | Tyr | Gly<br>340 | Ala | Asn | Ala | Gly | Thr<br>345 | Pro | Gly | Glu | His | Gly<br>350 | Asn | Thr |
| Pro | Leu | His<br>355 | Leu | Ala | Ile | Ser | Lys<br>360 | Asp | Asn | Met | Glu | Met<br>365 | Ile | Lys | Ala |
| Leu | Ile | Val<br>370 | Phe | Gly | Ala | Glu | Val<br>375 | Asp | Thr | Pro | Asn<br>380 | Asp | Phe | Gly | Glu |
| Thr<br>385 | Pro | Ala | Phe | Met | Ala<br>390 | Ser | Lys | Ile | Ser | Lys<br>395 | Gln | Leu | Gln | Asp | Leu<br>400 |
| Met | Pro | Ile | Ser | Arg<br>405 | Ala | Arg | Lys | Pro | Ala<br>410 | Phe | Ile | Leu | Ser | Ser<br>415 | Met |
| Arg | Asp | Glu | Lys<br>420 | Arg | Ile | His | Asp | His<br>425 | Leu | Leu | Cys | Leu | Asp<br>430 | Gly | Gly |
| Gly | Val | Lys<br>435 | Gly | Leu | Val | Ile | Ile<br>440 | Gln | Leu | Leu | Ile | Ala<br>445 | Ile | Glu | Lys |
| Ala | Ser<br>450 | Gly | Val | Ala | Thr | Lys<br>455 | Asp | Leu | Phe | Asp | Trp<br>460 | Val | Ala | Gly | Thr |
| Ser<br>465 | Thr | Gly | Gly | Ile | Leu<br>470 | Ala | Leu | Ala | Ile | Leu<br>475 | His | Ser | Lys | Ser | Met<br>480 |
| Ala | Tyr | Met | Arg | Gly<br>485 | Val | Tyr | Phe | Arg | Met<br>490 | Lys | Asp | Glu | Val | Phe<br>495 | Arg |
| Gly | Ser | Arg | Pro<br>500 | Tyr | Glu | Ser | Gly | Pro<br>505 | Leu | Glu | Glu | Phe | Leu<br>510 | Lys | Arg |
| Glu | Phe | Gly<br>515 | Glu | His | Thr | Lys | Met<br>520 | Thr | Asp | Val | Lys | Lys<br>525 | Pro | Lys | Val |
| Met | Leu<br>530 | Thr | Gly | Thr | Leu | Ser<br>535 | Asp | Arg | Gln | Pro | Ala<br>540 | Glu | Leu | His | Leu |
| Phe<br>545 | Arg | Asn | Tyr | Asp | Ala<br>550 | Pro | Glu | Val | Ile | Arg<br>555 | Glu | Pro | Arg | Phe | Asn<br>560 |
| Gln | Asn | Ile | Asn | Leu<br>565 | Lys | Pro | Pro | Thr | Gln<br>570 | Pro | Ala | Asp | Gln | Leu<br>575 | Val |
| Trp | Arg | Ala | Ala<br>580 | Arg | Ser | Ser | Gly | Ala<br>585 | Ala | Pro | Thr | Tyr | Phe<br>590 | Arg | Pro |
| Asn | Gly | Arg<br>595 | Phe | Leu | Asp | Gly | Gly<br>600 | Leu | Leu | Ala | Asn | Asn<br>605 | Pro | Thr | Leu |
| Asp | Ala<br>610 | Met | Thr | Glu | Ile | His<br>615 | Glu | Tyr | Asn | Gln | Asp<br>620 | Met | Ile | Arg | Lys |
| Gly<br>625 | Gln | Gly | Asn | Lys | Val<br>630 | Lys | Lys | Leu | Ser | Ile<br>635 | Val | Val | Ser | Leu | Gly<br>640 |
| Thr | Gly | Arg | Ser | Pro<br>645 | Gln | Val | Pro | Val | Thr<br>650 | Cys | Val | Asp | Val | Phe<br>655 | Arg |
| Pro | Ser | Asn | Pro<br>660 | Trp | Glu | Leu | Ala | Lys<br>665 | Thr | Val | Phe | Gly | Ala<br>670 | Lys | Glu |
| Leu | Gly | Lys<br>675 | Met | Val | Val | Asp | Cys<br>680 | Cys | Thr | Asp | Pro | Asp<br>685 | Gly | Arg | Ala |
| Val | Asp<br>690 | Arg | Ala | Arg | Ala | Trp<br>695 | Ser | Glu | Met | Val | Gly<br>700 | Ile | Gln | Tyr | Phe |
| Arg<br>705 | Leu | Asn | Pro | Gln | Leu<br>710 | Gly | Ser | Asp | Ile | Met<br>715 | Leu | Asp | Glu | Val | Asn<br>720 |
| Asp | Ala | Val | Leu | Val<br>725 | Asn | Ala | Leu | Trp | Glu<br>730 | Thr | Glu | Val | Tyr | Ile<br>735 | Tyr |
| Glu | His | Arg | Glu<br>740 | Glu | Phe | Gln | Lys | Leu<br>745 | Val | Gln | Met | Leu | Leu<br>750 | Ser | Pro |

( 2 ) INFORMATION FOR SEQ ID NO:3:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( x i ) SEQUENCE DESCRIPTION: SEQ ID NO:3:

```
Asn  Pro  His  Ser  Gly  Phe  Arg
1                   5
```

( 2 ) INFORMATION FOR SEQ ID NO:4:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( x i ) SEQUENCE DESCRIPTION: SEQ ID NO:4:

```
Xaa  Ala  Ser  Xaa  Gly  Leu  Asn  Gln  Val  Asn  Lys
1                   5                             10
```

( 2 ) INFORMATION FOR SEQ ID NO:5:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( x i ) SEQUENCE DESCRIPTION: SEQ ID NO:5:

```
Tyr  Gly  Ala  Ser  Pro  Leu  His  Xaa  Ala  Lys
1                   5                        10
```

( 2 ) INFORMATION FOR SEQ ID NO:6:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( x i ) SEQUENCE DESCRIPTION: SEQ ID NO:6:

```
Asp  Asn  Met  Glu  Met  Ile  Lys
1                   5
```

( 2 ) INFORMATION FOR SEQ ID NO:7:

( i ) SEQUENCE CHARACTERISTICS:
        ( A ) LENGTH: 5 amino acids
        ( B ) TYPE: amino acid
        ( C ) STRANDEDNESS: single (D) TOPOLOGY: linear (ii) MOLECULE TYPE: peptide (iii) HYPOTHETICAL: NO (xi) SEQUENCE DESCRIPTION: SEQ ID NO:7:

Gly Val Tyr Phe Arg
1               5

(2) INFORMATION FOR SEQ ID NO:8:

(i) SEQUENCE CHARACTERISTICS:
    (A) LENGTH: 7 amino acids
    (B) TYPE: amino acid
    (C) STRANDEDNESS: single
    (D) TOPOLOGY: linear (ii) MOLECULE TYPE: peptide (iii) HYPOTHETICAL: NO (xi) SEQUENCE DESCRIPTION: SEQ ID NO:8:

Met Lys Asp Glu Val Phe Arg
1               5

(2) INFORMATION FOR SEQ ID NO:9:

(i) SEQUENCE CHARACTERISTICS:
    (A) LENGTH: 7 amino acids
    (B) TYPE: amino acid
    (C) STRANDEDNESS: single
    (D) TOPOLOGY: linear (ii) MOLECULE TYPE: peptide (iii) HYPOTHETICAL: NO (xi) SEQUENCE DESCRIPTION: SEQ ID NO:9:

Glu Phe Gly Glu His Thr Lys
1               5

(2) INFORMATION FOR SEQ ID NO:10:

(i) SEQUENCE CHARACTERISTICS:
    (A) LENGTH: 10 amino acids
    (B) TYPE: amino acid
    (C) STRANDEDNESS: single
    (D) TOPOLOGY: linear (ii) MOLECULE TYPE: peptide (iii) HYPOTHETICAL: NO (xi) SEQUENCE DESCRIPTION: SEQ ID NO:10:

Val Met Leu Thr Gly Thr Leu Ser Asp Arg
1               5                   10

(2) INFORMATION FOR SEQ ID NO:11:

(i) SEQUENCE CHARACTERISTICS:
    (A) LENGTH: 9 amino acids
    (B) TYPE: amino acid
    (C) STRANDEDNESS: single
    (D) TOPOLOGY: linear (ii) MOLECULE TYPE: peptide (iii) HYPOTHETICAL: NO (xi) SEQUENCE DESCRIPTION: SEQ ID NO:11:

```
Xaa  Tyr  Asp  Ala  Pro  Glu  Val  Ile  Arg
1                   5
```

( 2 ) INFORMATION FOR SEQ ID NO:12:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( x i ) SEQUENCE DESCRIPTION: SEQ ID NO:12:

```
Phe  Asn  Gln  Asn  Ile  Asn  Leu  Lys  Pro  Pro  Thr  Gln  Pro  Ala
1                   5                             10
```

( 2 ) INFORMATION FOR SEQ ID NO:13:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( x i ) SEQUENCE DESCRIPTION: SEQ ID NO:13:

```
Xaa  Xaa  Gly  Ala  Ala  Pro  Thr  Tyr  Phe  Arg  Pro
1                   5                        10
```

( 2 ) INFORMATION FOR SEQ ID NO:14:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( x i ) SEQUENCE DESCRIPTION: SEQ ID NO:14:

```
Thr  Val  Phe  Gly  Ala  Lys
1                   5
```

( 2 ) INFORMATION FOR SEQ ID NO:15:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( x i ) SEQUENCE DESCRIPTION: SEQ ID NO:15:

```
Xaa  Trp  Ser  Glu  Met  Val  Gly  Ile  Gln  Tyr  Phe  Arg
1                   5                        10
```

METHODS COMPRISING CALCIUM INDEPENDENT CYTOSOLIC PHOSPHOLIPASE A/B ENZYMES

This application is a continuation of application Ser. No. 08/422,106, filed Apr. 14, 1995 Now U.S. Pat. No. 5,589,170; which was a divisional of application Ser. No. 08/281,193, filed Jul. 27, 1994 now U.S. Pat. No. 5,466,595.

The present invention relates to a purified calcium independent cytosolic phospholipase $A_2$/B enzymes which are useful for assaying chemical agents for anti-inflammatory activity.

BACKGROUND OF THE INVENTION

The phospholipase $A_2$ enzymes comprise a widely distributed family of enzymes which catalyze the hydrolysis of the acyl ester bond of glycerophospholipids at the sn-2 position. One kind of phospholipase $A_2$ enzymes, secreted phospholipase $A_2$ or $sPLA_2$, are involved in a number of biological functions, including phosphiolipid digestion, the toxic activities of numerous venoms, and potential antibacterial activities. A second kind of phospholipase $A_2$ enzymes, the intracellular phospholipase $A_2$ enzymes, also known as cytosolic phospholipase $A_2$ or $cPLA_2$, are active in membrane phospholipid turnover and in regulation of intracellular signalling mediated by the multiple components of the well-known arachidonic acid cascade. One or more $cPLA_2$ enzymes are believed to be responsible for the rate limiting step in the arachidonic acid cascade, namely, release of arachidonic acid from membrane glycerophospholipids. The action of $cPLA_2$ also results in biosynthesis of platelet activating factor (PAF).

The phospholipase B enzymes are a family of enzymes which catalyze the hydrolysis of the acyl ester bond of glycerophospholipids at the sn-1 and sn-2 positions. The mechanism of hydrolysis is unclear but may consist of initial hydrolysis of the sn-2 fatty acid followed by rapid $A_2$ and lysophosphiolipase (Saito et al., Methods of Enzymol., 1991, 197, 446; Gassama-Diagne et al., J. Biol. Chem., 1989, 264, 9470). Whether these two events occur at the same or two distinct active sites has not been resolved. It is also unknown if these enzymes have a preference for the removal of unsaturated fatty acids, in particular arachidonic acid, at the sn-2 position and accordingly contribute to the arachidonic acid cascade.

Upon release from the membrane, arachidonic acid may be metabolized via the cyclooxygenase pathway to produce the various prostaglandins and thromboxanes, or via the lipoxygenase pathway to produce the various leukotrienes and related compounds. The prostaglandins, leukotrienes and platelet activating factor are well known mediators of various inflammatory states, and numerous anti-inflammatory drugs have been developed which function by inhibiting one or more steps in the arachidonic acid cascade. Use of the present anti-inflammatory drugs which act through inhibition of arachidonic acid cascade steps has been limited by the existence of side effects which may be harmful to various individuals.

A very large industrial effort has been made to identify additional anti-inflammatory drugs which inhibit the arachidonic acid cascade. In general, this industrial effort has employed the secreted phospholipase $A_2$ enzymes in inhibitor screening assays, for example, as disclosed in U.S. Pat. No. 4,917,826. However, because the secreted phospholipase $A_2$ enzymes are extracellular proteins (i.e., not cytosolic) and are not specific for hydrolysis of arachidonic acid, they are presently not believed to participate directly in the arachidonic acid cascade. While some inhibitors of the small secreted phospholipase $A_2$ enzymes have anti-inflammatory action, such as indomethacin, bromphenacyl bromide, mepacrine, and certain butyrophenones as disclosed in U.S. Pat. No. 4,239,780, it is presently believed that inhibitor screening assays should employ cytosolic phospholipase $A_2$ enzymes which directly participate in the arachidonic acid cascade.

An improvement in the search for anti-inflammatory drugs which inhibit the arachidonic acid cascade was developed in commonly assigned U.S. Pat. No. 5,322,776, incorporated herein by reference. In that application, a cytosolic form of phospholipase $A_2$ was identified, isolated, and cloned. Use of the cytosolic form of phospholipase $A_2$ to screen for anti-inflammatory drugs provides a significant improvement in identifying inhibitors of the arachidonic acid cascade. The cytosolic phospholipase $A_2$ disclosed in U.S. Pat. No. 5,322,776 is a 110 kD protein which depends on the presence of elevated levels of calcium inside the cell for its activity. The $cPLA_2$ of U.S. Pat. No. 5,322,776 plays a pivotal role in the production of leukotrienes and prostaglandins initiated by the action of pro-inflammatory cytokines and calcium mobilizing agents. The $cPLA_2$ of U.S. Pat. No. 5,322,776 is activated by phosphorylation on serine residues and increasing levels of intracellular calcium, resulting in translocation of the enzyme from the cytosol to the membrane where arachidonic acid is selectively hydrolyzed from membrane phospholipids.

In addition to the $cPLA_2$ of U.S. Pat. No. 5,322,776, some cells contain calcium independent phospholipase $A_2$/B enzymes. For example, such enzymes have been identified in rat, rabbit, canine and human heart tissue (Gross, TCM, 1991, 2, 115; Zupan et al., J. Med. Chem., 1993, 36, 95; Hazen et al., J. Clin. Invest., 1993, 91, 2513; Lehman et al., J. Biol. Chem., 1993, 268, 20713; Zupan et al., J. Biol. Chem., 1992, 267, 8707; Hazen et al., J. Biol. Chem., 1991, 266, 14526; Loeb et al., J. Biol. Chem., 1986, 261, 10467; Wolf et al., J. Biol. Chem., 1985, 260, 7295; Hazen et al., Meth. Enzymol., 1991, 197, 400; Hazen et al., J. Biol. Chem., 1990, 265, 10622; Hazen et al., J. Biol. Chem., 1993, 268, 9892; Ford et al., J. Clin. Invest., 1991, 88, 331; Hazen et al., J. Biol. Chem., 1991, 266, 5629; Hazen et al., Circulation Res., 1992, 70, 486; Hazen et al., J. Biol. Chem., 1991, 266, 7227; Zupan et al., FEBS, 1991, 284, 27), as well as rat and human pancreatic islet cells (Ramanadham et al., Biochemistry, 1993, 32, 337; Gross et al., Biochemistry, 1993, 32, 327), in the macrophage-like cell line, $P388D_1$ (Ulevitch et al., J. Biol. Chem., 1988, 263, 3079; Ackermann et al., J. Biol. Chem., 1994, 269, 9227; Ross et al., Arch. Biochem. Biophys., 1985, 238, 247; Ackermann et al., FASEB Journal, 1993, 7(7), 1237), in various rat tissue cytosols (Nijssen et al., Biochim. Biophys. Acta, 1986, 876, 611; Pierik et al., Biochim. Biophys. Acta, 1988, 962, 345; Aarsman et al., J. Biol. Chem., 1989, 264, 10008), bovine brain (Ueda et al., Biochem. Biophys, Res. Comm., 1993, 195, 1272; Hirashima et al., J. Neurochem., 1992, 59, 708), in yeast (*Saccharomyces cerevisiae*) mitochondria (Yost et al., Biochem. International, 1991, 24, 199), hamster heart cytosol (Cao et al., J. Biol. Chem., 1987, 262, 16027), rabbit lung microsomes (Angle et al., Biochim. Biophys. Acta, 1988, 962, 234) and guinea pig intestinal brush-border membrane (Gassama-Diagne et al., J. Biol. Chem., 1989, 264, 9470).

It is believed that the calcium independent phospholipase $A_2$/B enzymes may perform important functions in release of arachidonic acid in specific tissues which are characterized by unique membrane phospholipids, by generating lysophospholipid species which are deleterious to membrane integrity or by remodeling of unsaturated species of membrane phospholipids through deacylation/reacylation mechanisms. The activity of such a phospholipase may well be regulated by mechanisms that are different from that of the cPLA$_2$ of U.S. Pat. No. 5,322,776. In addition the activity may be more predominant in certain inflamed tissues over others. Although the enzymatic activity is not dependent on calcium this does not preclude a requirement for calcium in vivo, where the activity may be regulated by the interaction of other protein(s) whose function is dependent upon a calcium flux.

SUMMARY OF THE INVENTION

In certain embodiments, the present invention provides compositions comprising a purified phospholipase enzyme characterized by (a) activity in the absence of calcium; (b) a molecular weight of 86 kD on SDS-PAGE; and (c) the presence of one or more amino acid sequences selected from the group consisting of NPHSGFR (SEQ ID NO:3), XAS-XGLNQVNK (SEQ ID NO:4) (X is preferably N or A), YGASPLHXAK (SEQ ID NO:5) (X is preferably W), DNMEMIK (SEQ ID NO:6), GVYFR (SEQ ID NO:7), MKDEVFR (SEQ ID NO:8), EFGEHTK (SEQ ID NO:9), VMLTGTLSDR (SEQ ID NO:10), XYDAPEVIR (SEQ ID NO:11) (X is preferably N), FNQNINLKPPTQPA (SEQ ID NO:12), XXGAAPTYFRP (SEQ ID NO:13) (X is preferably S), TVFGAK (SEQ ID NO:14), and XWSEM-VGIQYFR (SEQ ID NO:15) (X is preferably A), wherein X represents any amino acid residue. In other embodiments, the enzyme is further characterized by activity in a mixed micelle assay with 1-palmitoyl-2-[$^{14}$C]-arachidonyl-phosphatidylcholine(preferably a specific activity of about 1 $\mu$mol to about 20 $\mu$mol per minute per milligram, more preferably a specific activity of about 1 $\mu$mol to about 5 $\mu$mol per minute per milligram); by a pH optimum of 6; and/or by the absence of stimulation by adenosine triphosphate in the liposome assay.

In other embodiments, the invention provides isolated polynucleotides comprising a nucleotide sequence selected from the group consisting of: (a) the nucleotide sequence of SEQ ID NO:1; (b) a nucleotide sequence encoding the amino acid sequence of SEQ ID NO:2; (c) a nucleotide sequence encoding a fragment of the amino acid sequence of SEQ ID NO:2 having activity in a mixed micelle assay with 1-palmitoyl-2-[$^{14}$C]-arachidonyl-phosphatidylcholine; (d) a nucleotide sequence capable of hybridizing with the sequence of (a), (b) or (c) which encodes a peptide having activity in a mixed micelle assay with 1-palmitoyl-2-[$^{14}$C]-arachidonyl-phosphatidylcholine; and (e) allelic variants of the sequence of (a). Expression vectors comprising such polynucleotides and host cells transformed with such vectors are also provided by the present invention. Compositions comprising peptides encoded by such polynucleotides are also provided.

The present invention also provides processes for producing a phospholipase enzyme, said process comprising: (a) establishing a culture of the host cell transformed with a cPLA$_2$/B encoding polynucleotide in a suitable culture medium; and (b) isolating said enzyme from said culture. Compositions comprising a peptide made according to such processes are also provided.

Certain embodiments of the present invention provide compositions comprising a peptide comprising an amino acid sequence selected from the group consisting of: (a) the amino acid sequence of SEQ ID NO:2; and (b) a fragment of the amino acid sequence of SEQ ID NO:2 having activity in a mixed micelle assay with 1-palmitoyl-2-[$^{14}$C]-arachidonyl-phosphatidylcholine.

The present invention also provides methods for identifying an inhibitor of phospholipase activity, said method comprising: (a) combining a phospholipid, a candidate inhibitor compound, and a composition comprising a phospholipase enzyme peptide; and (b) observing whether said phospholipase enzyme peptide cleaves said phospholipid and releases fatty acid thereby, wherein the peptide composition is one of those described above. Inhibitor of phospholipase activity identified by such methods, pharmaceutical compositions comprising a therapeutically effective amount of such inhibitors and a pharmaceutically acceptable carrier, and methods of reducing inflammation by administering such pharmaceutical compositions to a mammalian subject are also provided.

Polyclonal and monoclonal antibodies to the peptides of the invention are also provided.

BRIEF DESCRIPTION OF THE FIGURES

FIG. 7: A 4–20% SDS-PAGE of lysates (5×10$^{10}$ cpm/lane) of $^{35}$S-methionine labelled COS cells transfected with, no DNA, pED (no insert), clone 9 reverse orientation, clones 9, 31 and 49; lanes 1–6, respectively. Molecular weight markers are indicated.

DETAILED DESCRIPTION OF THE INVENTION

Figure 1A:
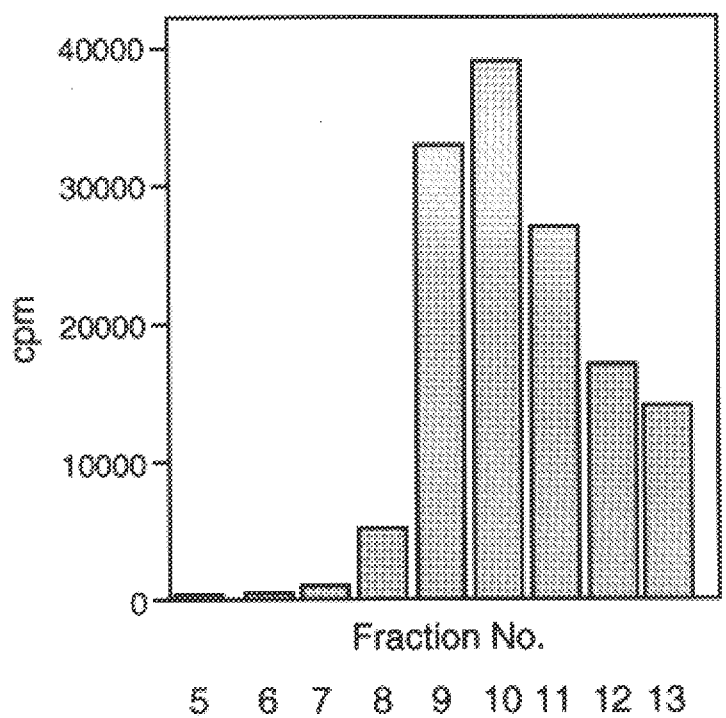
FIGS. 1A an 1B: Fractions containing activity eluted from a Mono P column were examined by reducing SDS-PAGE on a 4–20% gradient gel. Activity of each fraction is show above the gel and the 86 kD band is indicated on the silver stained gel. Molecular weight markers are indicated.
Figure 1B:
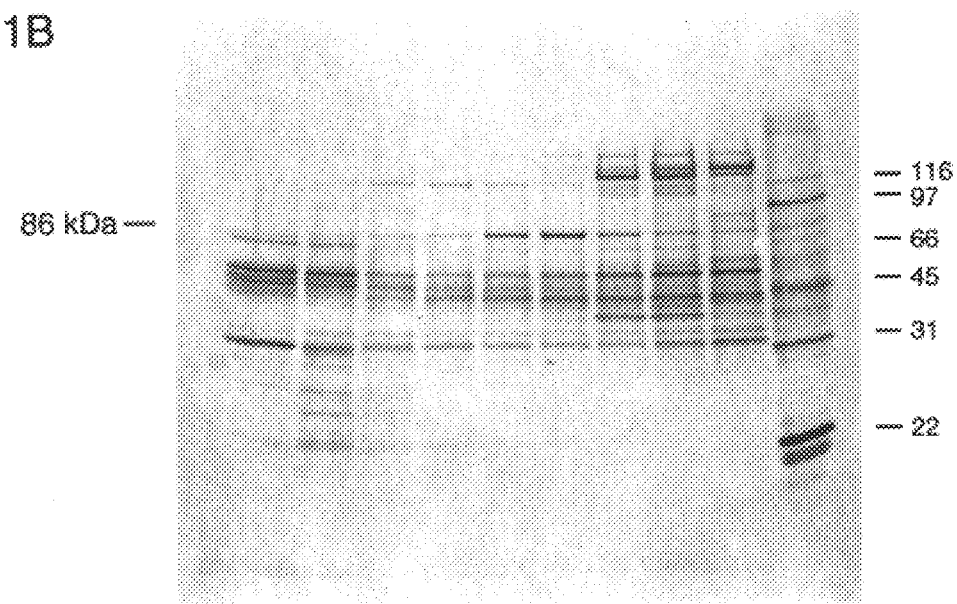
Figure 2A:
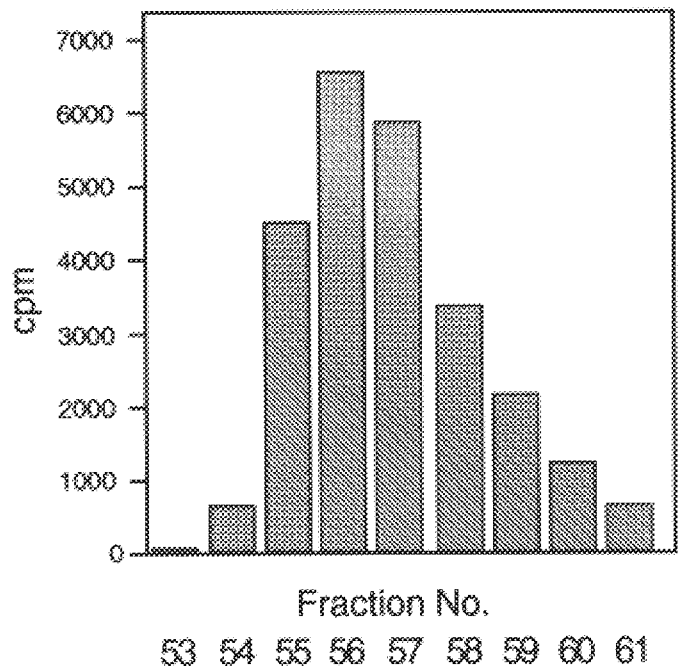
FIGS. 2A and 2B: Active fractions from a Mono p/Heparin column were combined and further purified on a size exclusion column. Activity eluted in the 250–350 kD size range. Examination of the fractions by SDS-PAGE under reducing conditions on 4–20% gel indicated only one protein band correlated with activity at 86 kD. Molecular weight markers are indicated.
Figure 2B:
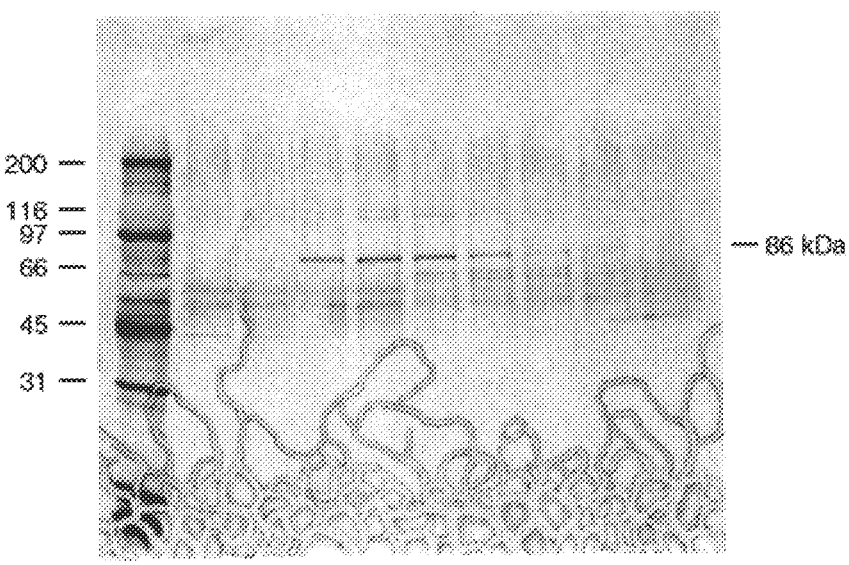
Figure 3A:
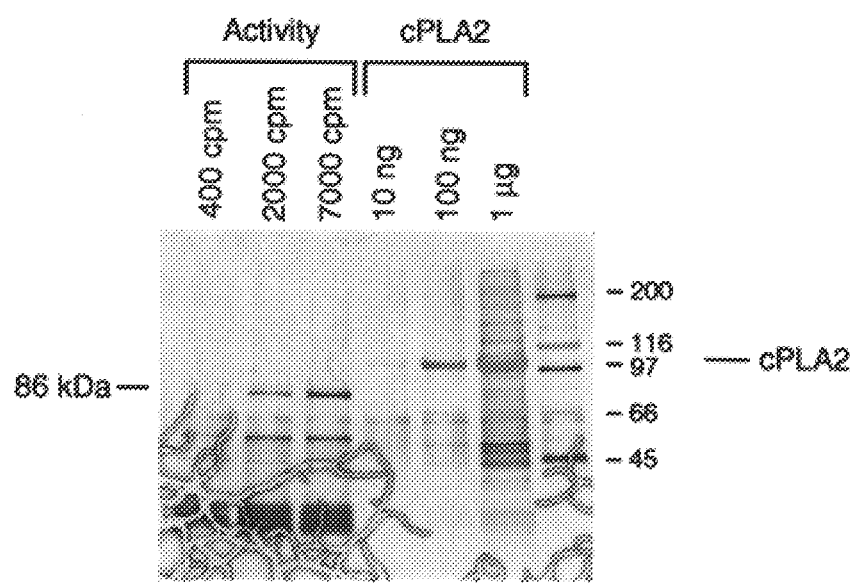
FIGS. 3A and 3B: Active fractions from Mono P eluate and cPLA$_2$ (0.1–1.0 $\mu$g) were analyzed on two 4–20% SDS gels under reducing conditions run in parallel. One gel was silver stained 3(A) and in the other gel the proteins were transferred to nitrocellulose. the blot was than probed with an anti-cPLA$_2$ polyclonal antibody and reactive proteins were visualized with the ECL system (Amersham) 3(B). Molecular weight markers are indicated.
Figure 3B:
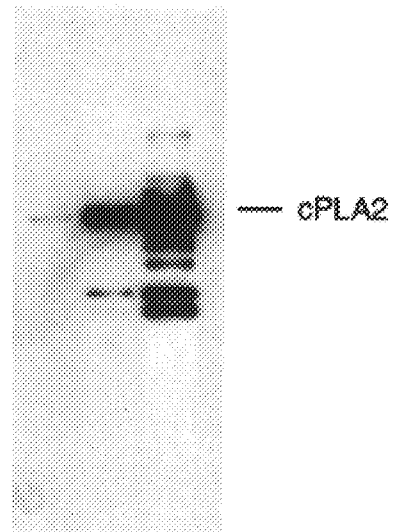
Figure 4:
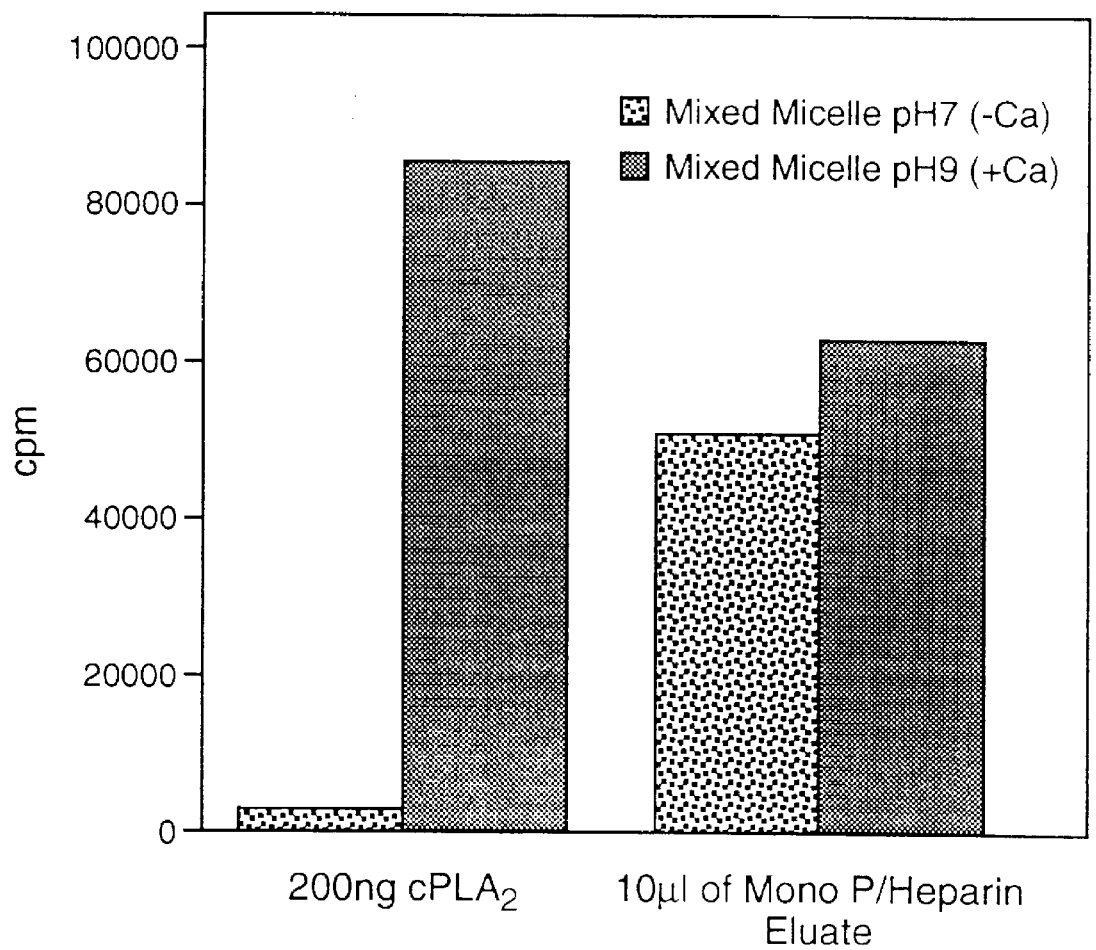
FIG. 4: The activity of the calcium-independent phospholipase eluted from a Mono P/Heparin column and cPLA$_2$ were compared under conditions which favor each enzyme; pH 7, 10% glycerol in the absence of calcium and pH 9, 70% glycerol in the presence of calcium, respectively.
Figure 5:
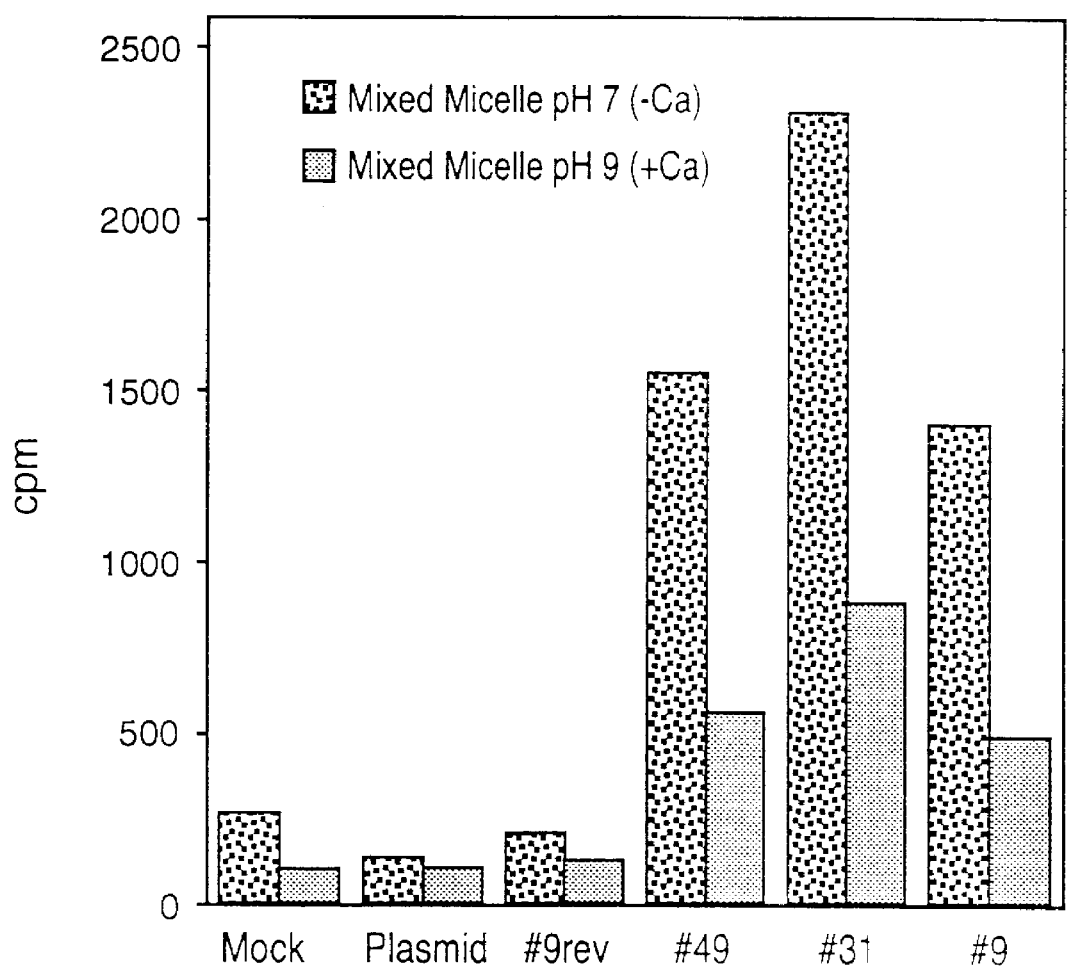
FIG. 5: Activity in the cytosolic extracts of COS cells transfected with: no DNA; plasmid (pED) containing no inserted gene; clone 9 in the antisense orientation; and clones 49, 31 and 9 expressed in pED. The extracts were analyzed under two different assay conditions described for the data presented in FIG. 4.
Figure 6:
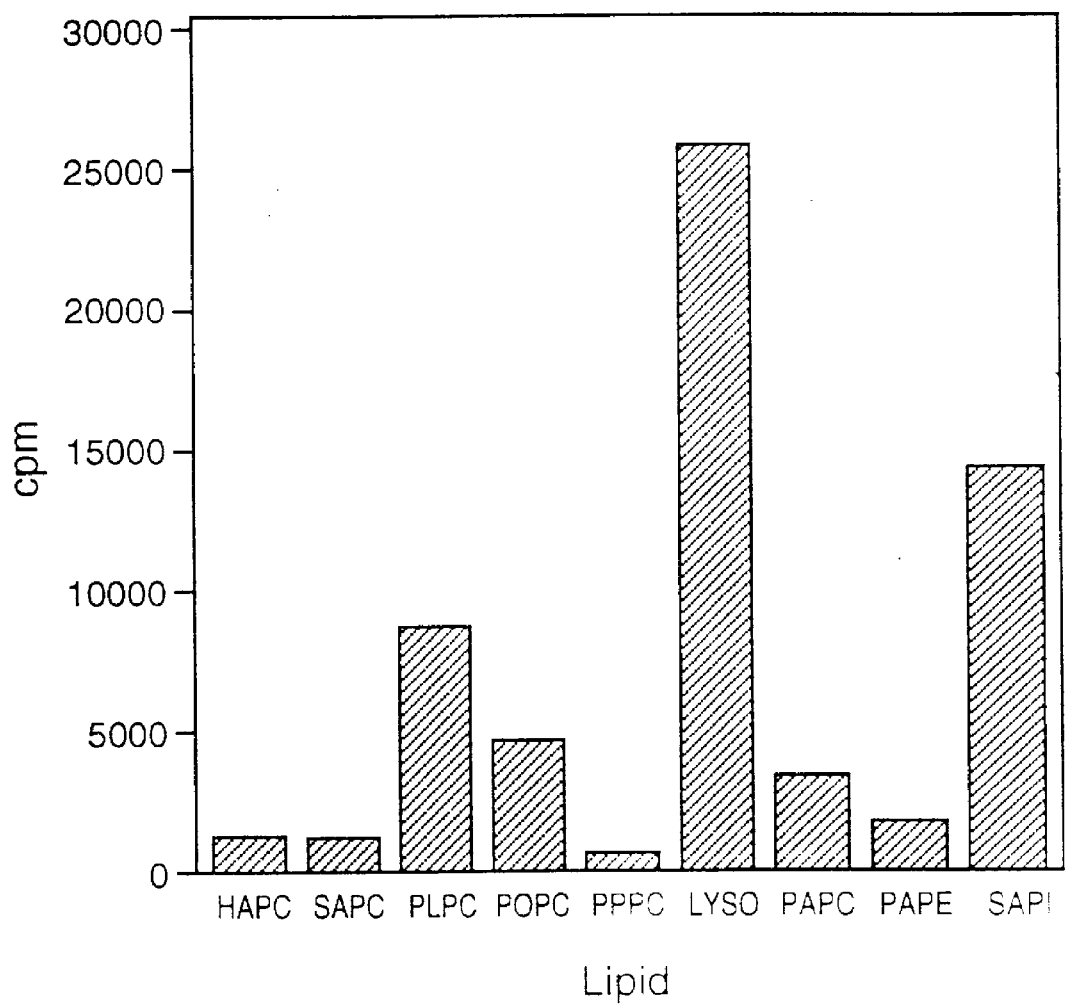
FIG. 6: A comparison of sn-2 fatty acid hydrolysis by activity eluted from a Mono P/Heparin column as a function of the fatty acid substituent at either the sn-1 or sn-2 position and the head group. HAPC, SAPC, PLPC, POPC, PPPC, LYSO and PAPC indicate 1-hexadecyl-2-arachidonyl-,1-stearoyl-2-arachidonyl-, 1--palmitoyl-2-linoleyl-,1-palmitoyl-2-oleyl-, 1 -palmitoyl-2-palmitoyl-, 1-palmitoyl-, 1 -palmitoyl-2-arachidonyl-phosphatidylcholine, respectively. PAPE and SAPI indicate 1-palmitoyl-2-arachidonyl-phosphotidylethanolamine and 1-stearoyl-2-arachidonyl-phosphoinositol, respectively. In all cases the $^{14}$C-labelled fatty acid is in the sn-2 position.

The present inventors have found surprisingly a calcium independent cytosolic phospholipase enzyme, designated calcium independent cytosolic phospholipase $A_2$/B or calcium independent $cPLA_2$/B, purified from the cytosol of Chinese hamster ovary (CHO) cells. The activity was also present in the cytosol of tissues and cell extracts listed in Table 1.

TABLE I

| tissue/cell | mixed micelle pH 7 (pmol/min/mg) | liposome pH 7 (pmol/min/mg) |
| --- | --- | --- |
| rat brain | | 1–2 |
| rat heart | | 0.3–0.5 |
| bovine brain | | 0.4 |
| pig heart | 0.8 | |
| CHO-Dukx | 10–20 | 2–5 |
| U937 (ATCC CRL1593) | 2 | |
| FBHE (ATCC CRL1395) | 2 | |
| H9c2 (ATCC Ccl 108) | 15 | |

The enzyme was originally purified by more than 8,000-fold from CHO cells by sequential chromatography on diethylaminoethane (DEAE), phenyl and heparin-toyopearl, followed by chromatofocussing on Mono P (as described further in Example 1). In addition the activity could be further purified by size exclusion chromatography after the Mono P column. The enzyme eluted from the size exclusion chromatography column in the 250–350 kD range, indicating the active enzyme may consist of a multimeric complex, or may possibly be associated with phospholipids.

The calcium independent phospholipase activity correlated with a single major protein band of 86 kD on denaturing sodium dodecyl sulfate polyacrylamide gel electrophoresis (SDS-PAGE) of active fractions from the Mono P and size exclusion chromatographic steps; in the latter no protein bands were observed in the 250–350 kD range. The specific activity of the enzyme is about 1 $\mu$mol to about 20 $\mu$mol per minute per milligram based on the abundance of the 86 kD band in the most active fractions eluted from the Mono P and size exclusion columns in the mixed micelle assay (Example 3B). The protein band was not recognized by a polyclonal antibody directed against the calcium dependent $cPLA_2$ of U.S. Pat. No. 5,322,776.

The calcium independent phospholipase of the present invention has a pH optimum of 6; its activity is suppressed by calcium (in all assays) and by triton X-100 (in the assay of Example 3A); and is not stimulated by adenosine triphosphate (ATP) (in the assay of Example 3A). The enzyme is inactivated by high concentration denaturants, e.g. urea above 3M, and by detergents, e.g. CHAPS and octyl glucoside. The calcium-independent phospholipase favors hydrolysis by several fold of unsaturated fatty acids, e.g. linoleyl, oleyl and arachidonyl, at the sn-2 position of a phospholipid compared with palmitoyl. In addition there is a preference for palmitoyl at the sn-1 position over hexadecyl or stearoyl for arachidonyl hydrolysis at the sn-2 position. In terms of head group substituents there is a clear preference for inositol over choline or ethanolamine when arachidonyl is being hydrolyzed at the sn-2 position. Further, as with $cPLA_2$ of U.S. Pat. No. 5,322,776, there is a significant lysophospholipase activity, i.e. hydrolysis of palmitoyl at the sn-1 position when there is no fatty acid substituent at the sn-2 position. Finally, hydrolysis of fatty acid substituents in the sn-1 or sn-2 in PAPC were compared where either palmitoyl or arachidonyl were labelled with $^{14}C$. Fatty acids were removed at both positions with the sn-2 position having a higher initial rate of hydrolysis by 2–3 fold. This result may indicate sequential hydrolysis of the arachidonyl substituent followed by rapid cleavage of palmitoyl in the lysophosphlolipid species, which is suggested by the hydrolysis of the individual lipid species. The similar rates of hydrolysis of fatty acid substituents at the sn-1 (palmitoyl) or sn-2 (arachidonyl) positions, where the radioactive label is in either position, is indicative of a phospholipase B activity. However, the fatty acid substituent at the sn-2 position clearly influences the PLB activity, not the sn-1 fatty acid, since hydrolysis of 1,2-dipalmitoyl substituted phospholipids is substantially less than for the 1-palmitoyl-2-arachidonyl species. These results can be clarified by studying the hydrolysis rates at each position of isotopically dual labelled phospholipids, e.g. $^3H$ and $^{14}C$ containing fatty acids at the sn-1 and sn-2 positions, respectively. Therefore, it is prudent to designate the enzyme as a phospholipase $A_2$/B.

A cDNA encoding the calcium independent $cPLA_2$/B of the present invention was isolated as described in Example 4. The sequence of the cDNA is reported as SEQ ID NO:1. The amino acid sequence encoded by such cDNA is SEQ ID NO:2. The invention also encompasses allelic variations of the cDNA sequence as set forth in SEQ ID NO:1, that is, naturally-occurring alternative forms of the cDNA of SEQ ID NO: 1 which also encode phospholipase enzymes of the present invention. Also included in the invention are isolated DNAs which hybridize to the DNA sequence set forth in SEQ ID NO:1 under stringent (e.g. 4×SSC at 65° C. or 50% formamide and 4×SSC at 42° C.), or relaxed (4×SSC at 50° C. or 30–40% formamide at 42° C. conditions.

The isolated polynucleotides of the invention may be operably linked to an expression control sequence such as the pMT2 or pFD expression vectors disclosed in Kaufman et al., Nucleic Acids Res. 19, 4485–4490 (1991), in order to produce the phospholipase enzyme peptides recombinantly. Many suitable expression control sequences are known in the art. General methods of expressing recombinant proteins are also known and are exemplified in R. Kaufman, Methods in Enzymology 185, 537–566 (1990). As defined herein "operably linked" means enzymatically or chemically ligated to form a covalent bond between the isolated polynucleotide of the invention and the expression control sequence, in such a way that the phospholipase enzyme peptide is expressed by a host cell which has been transformed (transfected) with the ligated polynucleotide/ expression control sequence.

A number of types of cells may act as suitable host cells for expression of the phospholipase enzyme peptide. Suitable host cells are capable of attaching carbohydrate side chains characteristic of functional phospholipase enzyme peptide. Such capability may arise by virtue of the presence of a suitable glycosylating enzyme within the host cell, whether naturally occurring, induced by chemical mutagenesis, or through transfection of the host cell with a suitable expression plasmid containing a polynucleotide encoding the glycosylating enzyme. Host cells include, for example, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, or HaK cells.

The phospholipase enzyme peptide may also be produced by operably linking the isolated polynucleotide of the invention to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the Max-Bac® kit), and such methods are well known in the art, as described in Summers and Smith, Texas Agricultural Experiment Station Bulletin No. 1555 (1987), incorporated herein by reference.

Alternatively, it may be possible to produce the phospholipase enzyme peptide in lower eukaryotes such as yeast or in prokaryotes such as bacteria. Potentially suitable yeast strains include *Saccharomyces cerevisiae, Schizosaccharomyces pombe*, Kluyveromyces strains, Candida, or any yeast strain capable of expressing heterologous proteins. Potentially suitable bacterial strains include *Escherichia coli, Bacillus subtilis, Salmonella typhimurium*, or any bacterial strain capable of expressing heterologous proteins. If the phospholipase enzyme peptide is made in yeast or bacteria, it is necessary to attach the appropriate carbohydrates to the appropriate sites on the protein moiety covalently, in order to obtain the glycosylated phospholipase enzyme peptide. Such covalent attachments may be accomplished using known chemical or enzymatic methods.

The phospholipase enzyme peptide of the invention may also be expressed as a product of transgenic animals, e.g., as a component of the milk of transgenic cows, goats, pigs, or sheep which are characterized by somatic or germ cells containing a polynucleotide encoding the phospholipase enzyme peptide.

The phospholipase enzyme peptide of the invention may be prepared by culturing transformed host cells under culture conditions necessary to express a phospholipase enzyme peptide of the present invention. The resulting expressed protein may then be purified from culture medium or cell extracts as described in the examples below.

Alternatively, the phospholipase enzyme peptide of the invention is concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred (e.g., S-Sepharose® columns). The purification of the phospholipase enzyme peptide from culture supernatant may also include one or more column steps over such affinity resins as concanavalin A-agarose, heparin-toyopearl® or Cibacrom blue 3GA Sepharose®; or by hydrophobic interaction chromatography using such resins as phenyl ether, butyl ether, or propyl ether; or by immunoaffinity chromatography.

Finally, one or more reverse-phase high performance liquid chromatography (RP-HPLC) steps employing hydrophobic RP-HPLC media, e.g., silica gel having pendant methyl or other aliphatic groups, can be employed to further purify the phospholipase enzyme peptide. Some or all of the foregoing purification steps, in various combinations, can also be employed to provide a substantially homogeneous isolated recombinant protein. The phospholipase enzyme peptide thus purified is substantially free of other mammalian proteins and is defined in accordance with the present invention as "isolated phospholipase enzyme peptide".

The calcium independent $cPLA_2/B$ of the present invention is distinct from the $cPLA_2$ of U.S. Pat. No. 5,322,776 and from previously-described calcium independent phospholipase $A_2$ enzymes (such as those described by Gross et al., supra; and Ackermann et al., supra). The enzyme of the present invention differs from the $cPLA_2$ of the '776 patent in the following ways:

(1) its activity is not calcium dependent;
(2) it is more active in 10% glicerol thin in 70% glycerol;
(3) it has a molecular weight 86 kD not 110 kD as for $cPLA_2$;
(4) it has a pH optimum of 6, not greater than 8 as for $cPLA_2$;
(5) it hydrolyzes fatty acids at sn-1 as well as sn-2;
(6) it binds to heparin, while $cPLA_2$ does not;
(7) it elutes from an anion exchange column at 0.1-0.2M NaCl, while $cPLA_2$ elutes at 0.3-0.4M NaCl; and
(8) it does not bind to anti-$cPLA_2$ polyclonal antibody. The enzyme of the present invention differs from the calcium independent enzyme of Gross et al. in the following characteristics:

(1) it has a molecular weight of 86 kD, not 40 kD as for the Gross enzyme;
(2) it is not homologous at the protein level to rabbit skeletal muscle phosphofructokinase in contrast to the 85 kD putative regulatory protein associated with the 40 kD Gross enzyme;
(3) hydrolysis at the sn-2 position is favored by an acyl-linked fatty acid at the sn-1 position in contrast to ether-linked fatty acids with the Gross enzyme;
(4) its does not bind to an ATP column and was not activated by ATP in a liposome assay compared to the Gross enzyme; and
(5) it was active in a mixed micelle assay containing Triton X-100. The enzyme of the present invention differs from the calcium independent enzyme of Ackermann et al. (the "Dennis enzyme")in the following characteristics:

(1) it does not bind to an ATP column;
(2) it binds to an anion exchange column (mono Q), while the Dennis enzyme remains in the unbound fraction;
(3) it has a molecular weight of 86 kD, not 74 kD as for the Dennis enzyme;
(4) it has substantial lysophospholipase activity and is relatively inactive on phospholipids containing ether-linked fatty acids at the sn-1 position in a liposome assay; and
(5) it appears to hydrolyze fatty acid substituents at the sn-1 and sn-2 positions of a phospholipid, whereas the Dennis enzyme favors hydrolysis at the sn-2 position.

The calcium independent $cPLA_2/B$ of the present invention may be used to screen unknown compounds having anti-inflammatory activity mediated by the various components of the arachidonic acid cascade. Many assays for phospholipase activity are known and may be used with the calcium independent phospholipase $A_2/B$ on the present invention to screen unknown compounds. For example, such an assay may be a mixed micelle assay as described in Example 3. Other known phospholipase activity assays include, without limitation, those disclosed in U.S. Pat. No. 5,322,776. These assays may be performed manually or may be automated or robotized for faster screening. Methods of automation and robotization are known to those skilled in the art.

In one possible screening assay, a first mixture is formed by combining a phospholipase enzyme peptide of the present invention with a phospholipid cleavable by such peptide, and the amount of hydrolysis in the first mixture ($B_0$) is measured. A second mixture is also formed by combining the peptide, the phospholipid and the compound or agent to be screened, and the amount of hydrolysis in the second mixture (B) is measured. The amounts of hydrolysis in the first and second mixtures are compared, for example, by performing a $B/B_o$ calculation. A compound or agent is considered to be capable of inhibiting phospholipase activity (i.e., providing anti-inflammatory activity) if a decrease in hydrolysis in the second mixture as compared to the first mixture is observed. The formulation and optimization of mixtures is within the level of skill in the art, such mixtures may also contain buffers and salts necessary to enhance or to optimize the assay, and additional control assays may be included in the screening assay of the invention.

Other uses for the calcium independent $cPLA_2/B$ of the present invention are in the development of monoclonal and polyclonal antibodies. Such antibodies may be generated by employing purified forms of the calcium independent $cPLA_2$ or immunogenic fragments thereof as an antigen using standard methods for the development of polyclonal and monoclonal antibodies as are known to those skilled in the art. Such polyclonal or monoclonal antibodies are useful as research or diagnostic tools, and further may be used to study phospholipase $A_2$ activity and inflammatory conditions.

Pharmaceutical compositions containing anti-inflammatory agents (i.e., inhibitors) identified by the screening method of the present invention may be employed to treat, for example, a number of inflammatory conditions such as rheumatoid arthritis, psoriasis, asthma, inflammatory bowel disease and other diseases mediated by increased levels of prostaglandins, leukotriene, or platelet activating factor. Pharmaceutical compositions of the invention comprise a therapeutically effective amount of a calcium independent $cPLA_2$ inhibitor compound first identified according to the present invention in a mixture with an optional pharmaceutically acceptable carrier. The term "pharmaceutically acceptable" means a non-toxic material that does not interfere with the effectiveness of the biological activity of the active ingredient(s). The term "therapeutically effective amount" means the total amount of each active component of the method or composition that is sufficient to show a meaningful patient benefit, i.e., healing or amelioration of chronic conditions or increase in rate of healing or amelioration. When applied to an individual active ingredient, administered alone, the term refers to that ingredient alone. When applied to a combination, the term refers to combined amounts of the active ingredients that result in the therapeutic effect, whether administered in combination, serially or simultaneously. A therapeutically effective dose of the inhibitor of this invention is contemplated to be in the range of about 0.1 $\mu$g to about 100 $\mu$g per kg body weight per application. It is contemplated that the duration of each application of the inhibitor will be in the range of 12 to 24 hours of continuous administration. The characteristics of the carrier or other material will depend on the route of administration.

The amount of inhibitor in the pharmaceutical composition of the present invention will depend upon the nature and severity of the condition being treated, and on the nature of prior treatments which the patient has undergone. Ultimately, the attending physician will decide the amount of inhibitor with which to treat each individual patient. Initially, the attending physician will administer low doses of inhibitor and observe the patient's response. Larger doses of inhibitor may be administered until the optimal therapeutic effect is obtained for the patient, and at that point the dosage is not increased further.

Administration is preferably intravenous, but other known methods of administration for anti-inflammatory agents may be used. Administration of the anti-inflammatory compounds identified by the method of the invention can be carried out in a variety of conventional ways. For example, for topical administration, the anti-inflammatory compound of the invention will be in the form of a pyrogen-free, dermatologically acceptable liquid or semi-solid formulation such as an ointment, cream, lotion, foam or gel. The preparation of such topically applied formulations is within the skill in the art. Gel formulation should contain, in addition to the anti-inflammatory compound, about 2 to about 5% W/W of a gelling agent. The gelling agent may also function to stabilize the active ingredient and preferably should be water soluble. The formulation should also contain about 2% W/V of a bactericidal agent and a buffering agent. Exemplary gels include ethyl, methyl, and propyl celluloses. Preferred gels include carboxypolymethylene such as Carbopol (934P; B.F. Goodrich), hydroxypropyl methylcellulose phthalates such as Methocel (K100M premium; Merril Dow), cellulose gums such as Blanose (7HF; Aqualon, U.K.), xanthan gums such as Keltrol (TF; Kelko International), hydroxyethyl cellulose oxides such as Polyox (WSR 303; Union Carbide), propylene glycols, polyethylene glycols and mixtures thereof. If Carbopol is used, a neutralizing agent, such as NaOH, is also required in order to maintain pH in the desired range of about 7 to about 8 and most desirably at about 7.5. Exemplary preferred bactericidal agents include steryl alcohols, especially benzyl alcohol. The buffering agent can be any of those already known in the art as useful in preparing medicinal formulations, for example 20 mN phosphate buffer, pH 7.5.

Cutaneous or subcutaneous injection may also be employed and in that case the anti-inflammatory compound of the invention will be in the form of pyrogen-free, parenterally acceptable aqueous solutions. The preparation of such parenterally acceptable solutions, having due regard to pH, isotonicity, stability, and the like, is within the skill in the art.

Intravenous injection may be employed, wherein the anti-inflammatory compound of the invention will be in the form of pyrogen-free, parenterally acceptable aqueous solutions. A preferred pharmaceutical composition for intravenous injection should contain, in addition to the anti-inflammatory compound, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition according to the present invention may also contain stabilizers, preservatives, buffers, antioxidants, or other additive known to those of skill in the art.

The amount of anti-inflammatory compound in the pharmaceutical composition of the present invention will depend upon the nature and severity of the condition being treated, and on the nature of prior treatments which the patient has undergone. Ultimately, the attending physician will decide the amount of anti-inflammatory compound with which to treat each individual patient.

Anti-inflammatory compounds identified using the method of the present invention may be administered alone or in combination with other anti-inflammation agents and therapies.

EXAMPLE 1

PURIFICATION OF CALCIUM INDEPENDENT cPLA$_2$

A) Preparation of CHO-Dukx cytosolic fraction

CHO cells, approximately $5 \times 10^{11}$ cells from a 250L culture, were concentrated by centrifugation and rinsed once with phosphate-buffered saline and reconcentrated. the cell slurry was frozen in liquid nitrogen and stored at $-80°$ C. at $4 \times 10^{11}$ cells/kg of pellet. The CHO pellets were processed in 0.5 kg batches by thawing the cells in 1.2L of 2 mM imidazol pH 7.5, 0.25M sucrose, 2 mM EDTA, 2 mM EGTA, 1 µg/ml leupeptin, 5 µg/ml aprotinin, 5 mM DTT and 1 mM PMSF ("Extraction Buffer"). The cells were transferred to a Parr bomb at $4°$ C. and pressurized at 600 psi for 5 minutes and lysed by releasing the pressure. The supernatant was centrifuged at 10,000×g for 30 minutes and subsequently at 100,000×g for 60 minutes.

B) DEAE anion exchange chromatography

The cytosolic fraction (10 gm protein) was diluted to 5 mg/ml with 20 mM imidazol pH 7.5, 5mM DTT, 1 mM EDTA and 1 mM EGTA (Buffer A) and applied to a 1L column of DEAE toyopearl equilibrated in buffer A at 16 ml/min. The column was washed to background absorbance ($A_{280}$) with buffer A and developed with a gradient of 0–0.5M NaCl in buffer A over 240 minutes with one minute fractions. The first activity peak at 100–150 mM NaCl was collected.

C) Hydrophobic interaction and heparin toyopearl chromatography

The DEAE fractions (4 gm of protein at 3 mg/ml) were made 0.5M in ammonium sulfate and applied at 10 ml/min to a 300 ml phenyl toyopearl column equilibrated in buffer A containing 0.5M ammonium sulfate. The column was washed to background absorbance ($A_{280}$). The column was then developed with a gradient of 0.5–0.2M (15 minutes) then 0.2–0.0M ammonium sulfate (85 minutes). The column was then connected in tandem to a 10 ml heparin column equilibrated in buffer A and elution was continued for 18 hours at 1.5 ml/min with buffer A. The phenyl column was disconnected and the activity was eluted from the heparin column by applying 0.5M NaCl in buffer A at 2 ml/min.

D) Chromatofocussing Chromatography

A portion of the above active fractions (16 mg) was dialyzed exhaustively against 20 mM Bis-Tris pH 7, 10% glycerol, 1M urea and 5 mM DTT and applied at 0.5 ml/min to a Mono P 5/20 column equilibrated with the same buffer. The column was washed with the same buffer to background absorbance ($A_{280}$) and a pH gradient was established by applying 10% polybuffer 74 pH 5, 10% glycerol, 1M urea and 5 mM DTT.

The relative purification of the enzyme of the present invention at each step of the foregoing purification scheme is summarized in Table II.

TABLE II

| Step | Protein (mg) | Activity (u**) | Specific Activity (u/mg) | Fold Purification | Yield (%) |
| --- | --- | --- | --- | --- | --- |
| cytosolic extract* | 126,000 | 2050 | 0.016 | — | — |
| DEAE | 16,000 | 1264 | 0.079 | 5 | 60 |
| phenyl/ heparin | 193 | 90 | 0.46 | 30 | 4.5 |
| Mono P | 0.1–0.2 | 14 | 140 | 8,000 | 0.7 |

*Extract from 3.5 kg of frozen CHO cell pellet
**1 unit is defined as the amount of activity that releases 1 nmol of arachidonic acid per minute The phospholipase can be further purified by the following steps:

E) Heparin chromatography

The sample from (D) above is applied at 0.5 ml/min onto a heparin column (maximum capacity 10 mg protein/ml of resin) equilibrated in buffer A. The activity is eluted by 0.4M NaCl in buffer A.

F) Size exclusion chromatography

The active fractions from the heparin column are applied to two TSK G3000SW$_{XL}$ columns (7.8 mm×30 cm) linked in tandem equilibrated with 150 mM NaCl in buffer A at 0.3 ml/min. Phospholipase activity elutes in the 250–350 kD size range.

Recombinant enzyme may also be purified in accordance with this example.

EXAMPLE 2

AMINO ACID SEQUENCING

A portion (63 µg total protein) of the Mono P active fractions was concentrated on a heparin column, as described above. The sample, 0.36 ml was mixed with an equal volume of buffer A and 10% SDS, 10 µl and concentrated to 40 µl on an Amicon-30 microconcentrator. The sample was diluted with buffer A, 100 µl, concentrated to 60 µl and diluted with Laemmli buffer (2x), 40 µl. The solution was boiled for 5 minutes and loaded in three aliquots on a 4–20% gradient SDS-PAGE mini gel. The sample was electophoresed for two hours at 120v, stained for 20 minutes in 0.2% Blue R-250, 20% methanol and 0.5% acetic acid and destained in 30% methanol (Rosenfeld et. al. Anal. Biochem. 203, pp. 173–179, 1992). Briefly, the protein bands corresponding to the phospholipase were excised from the gel with a razor blade and washed with 4 150 µl aliquots of 200 mM NH$_4$HCO$_3$, 50% acetonitrile, for a total of 2 hours. The gel pieces were allowed to air dry for approximately 5 minutes, then partially rehydrated with 1 µl of 200 mM NH$_4$HCO$_3$, 0.02% Tween 20 (Pierce) and 2 µl of 0.25 µg/µl trypsin (Promega). Gel slices were placed into the bottom of 500 µl mini-Eppendorf tubes, covered with 30 µl 200 mM NH$_4$HCO$_3$, and incubated at 37 C for 15 hours. After 1–2 minutes of centrifugation in an Eppendorf microfuge, the supernatants were removed and saved. Peptides in the gel slices were extracted by agitation for a total of 40 minutes with 2 100 µl aliquots of 60% acetonitrile, 0.1% TFA. The extracts were combined with the previous supernatant. The volume was reduced by lyophilization to about 150 µl, and then the sample was diluted with 750 µl 0.1% TFA. Peptide maps were run on an ABI 130A Separation System HPLC and an ABI 30×2.1 mm RP-300 column. The gradient used was as follows: 0–13.5 minutes 0% B, 13.5–63.5 minutes 0–100% B and 63.5–68.5 minutes 100% B, where A is 0.1% TFA and B is 0.085% TFA, 70% acetonitrile. Peptides were then sequenced on an ABI 470A gas-phase sequencer.

EXAMPLE 3

PHOPHOLIPASE ASSAYS 1. sn-2 Hydrolysis Assays

A) Liposome: The lipid, e.g. 1-palmitoyl-2-$[^{14}C]$ arachidonyl-sn-glycero-3-phosphocholine (PAPC), 55 mCi/mmol, was dried under a stream of nitrogen and solubilized in ethanol. The assay buffer contained 100 mM tris-HCl pH 7, 4 mM EDTA, 4 mM EGTA, 10% glycerol and 25 µM of labelled PAPC, where the volume of ethanol added was no more than 10% of the final assay volume. The reaction was incubated for 30 minutes at 37° C. and quenched by the addition of two volumes of heptane:isopropanol:0.5M sulfuric acid (105:20:1 v/v). Half of the organic was applied to a disposable silica gel column in a vacuum manifold positioned over a scintillation vial, and the free arachidonic was eluted by the addition of ethyl ether (1 ml). The level of radioactivity was measured by liquid scintillation.

Variations on this assay replace EDTA and EGTA with 10 mM $CaCl_2$.

B) Mixed Micelle Basic: The lipid was dried down as in (A) and to this was added the assay buffer consisting of 80 mM glycine pH 9, 5 mM $CaCl_2$ or 5 mM EDTA, 10% or 70% glycerol and 200 µM triton X-100. The mixture was then sonicated for 30–60 seconds at 4° C. to form mixed micelles.

C) Mixed Micelle Neutral: As for (B) except 100 mM Tris-HCl pH 7 was used instead of glycine as the buffer.

2. sn-1 Hydrolysis Assays

Sn-1 hydrolysis assays are performed as described above for sn-1 hydrolysis, but using phospholipids labelled at the sn-1 substituent, e.g. 1-$[^{14}C]$-palmitoyl-2-arachidonyl-sn-glycero-3 -phophocholine.

EXAMPLE 4

CLONING OF CALCIUM INDEPENDENT cPLA$_2$/B

A) cDNA Library Construction

Total RNA was first prepared from $2\times10^8$ CHO-DUX cells using the RNAgents total RNA kit (Promega, Madison, Wis.) and further purified using the PolyATract mRNA Isolation System (Promega) to yield 13.2 µg polyA+mRNA. Double stranded cDNA was prepared by the Superscript Choice System (Gibco/BRL, Gaithersburg, Md.) starting with 2 µg of CHO-DUX mRNA and using oligo dT primer. The cDNA was modified at both ends by addition of an EcoRI adapter/linker provided by the kit. These fragments were then ligated into the predigested lambda ZAPII/EcoRI vector, and packaged into phage particles with Gigapack Gold packaging extracts (Stratagene, La Jolla, Calif.).

B) Oligonucleotide Probe Design

Several of the peptide sequences determined for the purified calcium independent PLA$_2$/B were selected to design oligonucleotide probes. The amino acid sequence from amino acid 361 to 367 of SEQ ID NO:2 was used to design two degenerate oligonucleotide pools of 17 residues each. Pool 1 is 8-fold degenerate representing the sense strand for amino acids 361 to 366 of SEQ ID NO:2, and pool 2 is 12-fold degenerate representing the antisense strand for amino acids 362–367 of SEQ ID NO:2. Two other degenerate pools were also made from other sequences. Pool 3 is 32-fold degenerate and represents the sense strand for amino acids 490 to 495 of SEQ ID NO:2, and pool 4 is 64-fold degenerate representing the antisense strand for amino acids 513 to 518 of SEQ ID NO:2.

C) Library Screening

Approximately 400,000 recombinant bacteriophage from the CHO-DUX cDNA library were plated and duplicate nitrocellulose filters were prepared. One set of filters was hybridized with pool 1 and the other with pool 2 using tetramethylammonium chloride buffer conditions (Jacobs et al., Nature, 1985, 313, 806). Twelve positive bacteriophages were identified and plated for further analysis. Three sets of nitrocellulose filters were prepared from this plating and hybridized with pools 2, 3 and 4, to represent the three peptide sequences from which probes were designed. Several clones were positive for all three pools. Individual bacteriophage plaques were eluted and ampicillin resistant plasmid colonies were prepared following the manufacturer's protocols (Stratagene). Plasmid DNA was prepared for clones 9, 17, 31 and 49, and restriction digests revealed 3.0 kb inserts. Analysis of a portion of the DNA sequence in these clones confirmed that they contained several cPLA$_2$/B peptide sequences and represented the complete coding region of the gene. Clone 9 was selected for complete DNA sequence determination. The sequence of clone 9 is reported as SEQ ID NO:1.

Clone 9 was deposited with ATCC on Jul. 27, 1994 as accession number 69669.

EXAMPLE 5

EXPRESSION OF RECOMBINANT cPLA$_2$/B

A) Expression in COS Cells

Clone 9 from Example 4 was excised inserted into a SalI site that was engineered into the EcoRI site of the COS expression vector, PMT-2, a beta lactamase derivative of p 91023 (Wong et al., Science, 1985, 228, 810). 8 µg of plasmid DNA was then transfected into $1\times10^6$ COS cells in a 10 cm dish by the DEAE dextran protocol (Sompayrac et al., Proc. Natl. Acad. Sci. USA, 1981, 78, 7575) with the addition ol a 0.1 mM chloroquine to the transfection medium, followed by incubation for 3 hours at 37° C. The cells were grown in conventional media (DME, 10% fetal calf serum). At 40-48 hours post-transfection the cells were washed twice and then incubated at 37° C. in PBS, 1 mM EDTA (5 ml). The cells were then collected by centrifugation, resuspended in Extraction Buffer (0.5 ml), and lysed by 20 strokes in a Dounce at 4° C. The lysate was clarified by centrifugation and 10–50 µl of the cytosolic fraction was assayed in the neutral and pH 9 mixed micelle assays.

In a further experiment, COS cells were transiently transfected according to established procedures (Kaufman et al.). After 40–48 hours post-transfection the cells were labelled with $^{35}$S-methionine, 200 µCi per 10 cm plate, for one hour and the cells were lysed in NP-40 lysis buffer (Kaufman et al.). The cell lysates were analyzed by SDS-PAGE on a 4–20% reducing gel where equal counts were loaded per lane. There was an additional protein band at 84–86 kD in the lysates from cells transfected with clones 9, 31 and 49, but not in controls (see FIG. 7).

B) Expression in CHO Cells

A single plasmid bearing both the cPLA$_2$/B encoding sequence and a DHFR gene, or two separate plasmids bearing such sequences, are introduced into DHFR-deficient CHO cells (such as Dukx-BII) by calcium phosphate coprecipitation and transfection. DHFR expressing transformants are selected for growth in alpha media with dialyzed fetal calf serum. Transformants are checked for expression of recombinant enzyme by bioassay, immunoassay or RNA blotting and positive pools are subsequently selected for amplification by growth in increasing concentrations of methotrexate (MTX) (sequential steps in 0.02, 0.2, 1.0 and 5 μM MTX) as described in Kaufman et al., Mol. Cell Biol., 1983, 5, 1750. The amplified lines are cloned and recombinant enzyme expression is monitored by the mixed micelle assay. Recombinant enzyme expression is expected to increase with increasing levels of MTX resistance.

Patent and literature references cited herein are incorporated by reference as if fully set forth.

What is claimed is:

1. A method for identifying an inhibitor of phospholipase activity, said method comprising:

(a) combining a phospholipid, a candidate inhibitor compound, and a composition comprising a phospholipase enzyme peptide; and (b) observing whether said phospholipase enzyme peptide cleaves said phospholipid and releases fatty acid thereby, wherein said composition comprises a peptide selected from the group consisting of a peptide comprising the amino acid sequence of SEQ ID NO:2 and a peptide encoded by a polynucleotide comprising a nucleotide sequence selected from the group consisting of:

(1) the nucleotide sequence of SEQ ID NO:1;

(2) a nucleotide sequence encoding the amino acid sequence of SEQ ID NO:2; and (3) allelic variants of the sequence of (1).

2. The method of claim 1, wherein said peptide comprises the amino acid sequence of SEQ ID NO:2.

3. The method of claim 1, wherein said peptide comprises a peptide encoded by a polynucleotide comprising the nucleotide sequence of SEQ ID NO: 1.

4. The method of claim 1, wherein said peptide comprises a peptide encoded by a polynucleotide encoding the amino acid sequence of SEQ ID NO:2.

* * * * *